US007132528B2

(12) United States Patent
Heck et al.

(10) Patent No.: US 7,132,528 B2
(45) Date of Patent: Nov. 7, 2006

(54) PROMOTER FROM THE RICE TRIOSEPHOSPHATE ISOMERASE GENE OSTPI

(75) Inventors: Gregory R. Heck, Crystal Lake Park, MO (US); Jinsong You, Manchester, MO (US); Scott R. Baerson, Oxford, MS (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/911,373

(22) Filed: Aug. 4, 2004

(65) Prior Publication Data

US 2005/0108786 A1 May 19, 2005

Related U.S. Application Data

(60) Provisional application No. 60/493,972, filed on Aug. 8, 2003.

(51) Int. Cl.
*C12N 15/82* (2006.01)
*C07H 21/04* (2006.01)
*A01H 1/05* (2006.01)

(52) U.S. Cl. .................. 536/24.1; 435/320.1; 435/419; 435/468; 800/278

(58) Field of Classification Search ...................... None
See application file for complete search history.

(56) References Cited

U.S. PATENT DOCUMENTS 5,959,176 A * 9/1999 Torikai et al. .............. 800/287

OTHER PUBLICATIONS

Kim et al. A 20 nucleotide upstream element is essential for the nopaline synthase (nos) promoter activity. (1994) Plant Molecular Biology, vol. 24, pp. 105-117.*
Pater et al. The promoter of the rice gene GOS2 is active in various different monocot tissues and binds rice nuclear factor ASF-1. (1992) The Plant Journal, vol. 2, pp. 837-844.*
Database EMBL Sequence Library EBI, Hinxton; Oct. 5, 2000, T. Sasaki, et al., "Oryza Sativa (Japonica Cultivar-Group) Genomic DNA, Chromosome 1, PAC Clone:P0416D03, contains EST(s):C97863(C0030) note contains full-length cDNA(s): AK060920 gene P0416D03.44 product putative triosephosphate isomerase" XP-002303517 retrieved from EBI.AC.UK Database Accession No. AP002872 Abstract.
Database EMBL Sequence Library EBI, Hinxton; Jun. 12, 1993, Y. Xu, et al., "Oryza Sativa Triosephosphate Isomerase (Rictipi2) Gene, Exons 1-9—Genomic DNA" XP002303518 retrieved from EBI.AC.UK.Database Accession No. L04967 Abstract.
Yong Xu et al., "Rice Triosephosphate Isomerase Gene 5' Sequence Directs Beta-Glucuronidase Activity in Transgenic Tobacco But Requires An Intron For Expression in Rice", *Plant Physiology (Rockville)*, vol. 106, No. 2, pp. 459-467 (1994) XP002303513 ISSN: 0032-0889 Abstract.
Kimberly C. Snowden et al., "Intron Position Affects Expression From the TPI Promoter in Rice", *Plant Molecular Biology*, vol. 31, No. 3, pp. 689-692 (1996) XP002303514 ISSN: 0167-4412 the whole document.
Yong Xu et al., "Cytosolic Triosephosphate Isomerase Is a Single Gene Rice", *Plant Physiology (Rockville)*, vol. 101, No. 2, pp. 683-687 (1993) XP002303515 ISSN: 0032-0889 cited in the application.
T.C. Hall et al., "Transgene Expression and Agronomic Improvement of Rice", *Philosophical Transaction of the Royal Society of London B Biological Sciences*, vol. 342, No. 1301, pp. 197-201 (1993) XP008037969 ISSN: 0962-8436.
Yong Xu et al., "Isolation of a Triosephosphate Isomerase Gene and a Root-Specific Gene From Rice, and Analysis of Their Regulatory Sequences in Transgenic Rice and Tobacco", *Plant Physiology (Rockville)*, vol. 102, No. 1 Suppl., p. 72 (1993) XP002303516 *Joint Annual Meeting of the American Society of Plan: Minneapolis, Minnesota, USA*; Jul. 31-Aug. 4, 1993 ISSN: 0032-0889 the whole document.
International Search Report, PCT/US2004/024118 (Nov. 29, 2004).

* cited by examiner

*Primary Examiner*—Anne Kubelik
*Assistant Examiner*—Cathy Kingdon Worley
(74) *Attorney, Agent, or Firm*—Forchisa M. Davis; Howrey LLP

(57) ABSTRACT

The present invention relates to polynucleotide molecules for regulating gene expression in plants. In particular, the invention relates to DNA sequences of the rice (*Oryza sativa* cv Nipponbare) triosephosphate isomerase (OsTPI) gene promoter that are useful for regulating gene expression of heterologous polynucleotide molecules in plants. The invention also relates to expression constructs and transgenic plants containing the heterologous polynucleotide molecules operably linked to and regulated by OsTPI DNA sequences.

18 Claims, 4 Drawing Sheets

Figure 1A

```
   1 AAGCTTTAAT ATTACAAATT TTAAATAAAT AAATTTATTT CTTATTTTAA AGTAACTTTT
  61 ATATTAAATT TTTCGTACGG AACATACGGT TTAGTAGTTT AATTTTTTTT CCGACGTAGA
 121 ATCTGCATAT TCATTAGAAA AGAACGGGCT AGTTGTTGAG TCCACTATAG ACTCTTAAAT
 181 AGGCCATGTT AGAGAAAAAC GATAGTTCTG TAAAGGCCGG CTTTCTGATC GTCTCTCTAC
 241 TAGTAATACG CAATAATTAA ATTCTTGTAG CAAGTGCCAT GATTTTCTAC ATTTTGGATC
 301 TAAATACGTG ACTTTTCTTG TAGATGGACT ATACAACGGC CGTTGCTTAT CTCGTCTGCT
 361 CTTGTTTTTC TCGTTGTGAG CCGGTGTCAG GCTGATGGCA TGCAAAACAT CCCTGCATGC
 421 ATCTTCCTTC TTGGTTCTTT CTCTTCCACA TCATCAAATT TGTTTACATA ATAATAAATA
 481 GAGCGCATCT TCCTTCTTTG TTTCTTTCTC TTCCACATCA TCAAATTTAT TTACTTAACA
 541 ATAAATAGAG CCCATTGATT AATACCTTTG TACATGCCCT TACGCGGGAA GGAATCGACG
 601 ACAATGGTGC GCATGGACCA ACGTGGCTAT ACATCAGCGA CGACAACTCA CAACCGCGAA
 661 GCAATGTAAA CGCAGTAGCA TCTAAATAGG TAACGACAAA GATGTTCACT AATCTCCAAT
 721 TTGTAGTTTG TAGCTAGTAG CATATCATCC CAGACGGGCA TATCGCGGTT ATAAATAACC
 781 AGCGATGGTC CAATTAGTTT GTCCAATTAC TTTCACGAGT TAATCCCGAT CATTCCAGGA
 841 TTAATATATA GCAGGTGCAC AATACACATC GGTCTCAAAC GGCCTTCCTT TTAGACAACT
 901 AATTATACAA GAGATATGTA ATAATTAGG TGAACCCATC GATCAAAAGC ATCACGACCT
 961 TACCTATAGA GCTAAAGCCT CCAATGGCGA GAGAGTTGGT GAGTAAAGAG CAGATGACAC
1021 AGAACGCATA TGTACACATG ATTGTTTCTT CTAGACGATG GTCTTTCCTG GCTTGAATAA
1081 TGATGTTTTA TAGTAGTATT CCACTAATAA TTAATAAATA TCCCTAGTTG GTCATCTTCC
1141 CGACGACTAA GCGGTCAACC TAAGCACTCA ACAGCTACTA GTACTAATGA ATGTCGATCT
1201 GCATGTGCTT CCTGATGTGA CACTAATGAT TGATTAATTT AAGACTATAT GATGTTGAAG
1261 ATTGAACCAC CCAAATTCTC TACCCATTTA TATTTATTCC CTAATACAAT GAAGCATGCA
1321 TTTATTTCTA GACTAGAGAC ATTTAATTAT TTTGCCACTC TTAAATGTGG TAAGTAACCA
1381 TTTACCATGT ATACCCACAT GTCATAGACA CGTAAGGATC CAAATGTTAA CACATAGGTG
1441 TCAGATAGTT AAACGTCTAA CCTAAAAGTA ACAAATATTT AAATATCCCT TATATCTATG
1501 ATTGAAAGGA AAAAAGTCTA AGTACAATTG TCGAGATATG GCAGGTTTGG TAGGTCTCTA
1561 ACTTCTCAAC TTAACTCAAA TAATTAAGTT TAGAGTGGAA TTATGGAGCA CCTTGAATCC
1621 AGATTCATCT CTCTAATTTG TTTTAATAGC ACTGCTCTAC TCCCTTTTAG ATGGAATTGA
1681 AATCGTTTGG TTGGACTTCA TCCCTAACCT CCATAAGAGG TGAAATTGGA GCTAGAAGTA
1741 TGTCAAACAT GGCCATATAA TCTAAGAACA GCTTATCGAG ATATCCAACA AAAATAATC
1801 GTTCTCCTAT TTCAGTGAGT AAAAACCTGA TGGTCCAAAC GAGTTGGGCT GAAAATGGGA
1861 CAGTGTTTCG GTGAGACGGG CCCAGCAAGA ACATAGGCCT GGTTGGGCCC CTATTCCCCC
1921 TACGTTTTCT CGGCCCACCC ACCGTTGGGC TCGGCTCGGG CCTACCATCG GGCGGAGAGG
1981 AGGCCCAACT CGGGAAAAAG GAGAAACAGA AAAGAGGCCG AAAAGGCGAA AGGGATCGAT
2041 GAGGTGGGGA CCACCGGACC AGCGAGAGAT GCGCATCCCG ATGCAGCACG ATGCCGCGGC
2101 GCCCTCTGTT CCGCTCCGCG CCGCGGCCAC GAAAACCACG ACGCCGCCGG GATCATCTGC
2161 GTCCGCCTTA CCAGTGGCCC TCGCTGCTAT GGATGACTTA AGCAGTTTTT TTTATGTGTA
2221 TAAATAAAAC AGGGTAGTTA ACGAGTCATA CTTTGTTTCT GGAAGAGAAT ATCTTTTTAG
2281 GAAAAAAGCA ATAGGTCATC TTACTCTTTG CTACAGGTGC AATAATTTGC CCGGACAATA
2341 GACCTGAGTA TAGTTTATTT AGTTCTAAAC AATGCATCAG AATATGGAGG AAAAAGATGG
2401 CCTTAGTATA GGATCAATTG AGATGTACAG TTAAACAAAA AAGTAGATAT GGATTTACAA
2461 AATTGATGCG GAATATTATA TCCATGTAGT AGCTCCCATG TACTAGTTTC TTTTGCTTGA
2521 AAAAATAAAA GAAGCAGATA ATTTCTAGAG AAGTCCAGAG AATAAAAGA TTGGTGGTGG
2581 GAGTGGGACC CACCTGTCAT TGTCGGAGGA GCCTGCCTCG CCTCATGTGA TCCCATCGGA
2641 GGCCACACCT CTGCTCCCCC TATATTATCC TGTCCATGGT GTTTTCTTC CTCCTCCACA
2701 AAAACCAAAA TCCAATCTCC AGCTCTCTTC CCCCCCCCCC CCCCCCGCG TCCAGTTCCA
2761 TCTAATCAGC TTCTCGTCGA GATAGGCCGC AAGTTCTTCG TTGGTGGCAA CTGGAATTGC
2821 GTAATTTTTT TCTCTTCCTG CTTGAAATCT CTAGTCGCAT GTTCTTGTGT CTCGGTGACT
2881 CAGGAGAATT TTTGATTTTT TTTTCTGTTC TGGAACGCGA TTTAGGGAGT GTTCGTTAGG
2941 TGGAGATAGG AGAGATTGTC TCTCGTTTTC CGCGCGCACG CTTTTCAAAC TACTAAACGG
3001 TGCGTTTTTT GCAAAAAATT TCAATAGGAA AGTTGCTTTA AAAAATCATA TTAATCCATT
```

Figure 1B

```
3061 TTTGAAATTT AAAATAGTTA ATACTCAATT AATCATGAGC TAATGGCTTA CCTCGTTTTG
3121 CGTATCTTCC CAATCTCCTC AATCCCCTTC TCTTCAAACA CTCCCTTAGT GATTTAAGGG
3181 TGGAGATTGC CATGAAGGGG ATGGATCTTT TTTTTTTTCT TGAAACATTA GGAGAGATTT
3241 TTCCACGCTG ATCCAGATCG GTGTAGAAAC CACCCTGGTT GGTTGAGAAG AATGGATGGA
3301 TGGCGGGGTT TTTGAGATCC GGATAATATA TCTGAAGATT TGGTCTTCGT TTTCAGTCCG
3361 GTCCTAATCC TAGGAACCAG ATGCGATTAG CTGCTACATA TGCTACTCCT ACACGATTAG
3421 CCGCGTTTTT TGGCGTTTCA ACGCGAGACA CTCTTAGTGG GAAATTTGGA GTTCACTGAT
3481 CTTCAGGTGT TCCATCTTGC GCAAAGTGTG ATGTCGGGTA TGTTTAGCTC GGTTCAGACT
3541 TCAGAGTCTG AAACTTTTAT GAGGTGCATG CGTGTATTAT CCAGTGTCTA GAATTTGTCT
3601 CTGACGTGAA TTATCAAGTG TCTAGAATTT AAGTCAGATC AAGGAGCCAA CACCCGGAGA
3661 TTTATTAATC AAATGGTGCA TATTAGCTTT TGTCAATCGT GATTTCTAGC TTTGAACTGT
3721 TGTTAACTTA CACAAGAAAC GCGTCATGCA CTTGGAGAAC GGTAGTGGTA TTGATGCTTC
3781 TTGTCGAATT TCTCGTATGC ATATATGCTG AGAAATGCGA AAGAAAAGCA CGGGTATTTT
3841 GTGTGATTTC AATGTCGTAG TGTGGTCTGT ATCAATCTTC AAATATTTGC TTGCTAAAGA
3901 CTGACATGAT TCATTTTGAT GTAATAGAAC GGGACCATGG
```

PROMOTER FROM THE RICE TRIOSEPHOSPHATE ISOMERASE GENE OSTPI

This application claims benefit of U.S. Provisional Application No. 60/493,972, filed Aug. 8, 2003.

INCORPORATION OF THE SEQUENCE LISTING

Two copies of the sequence listing (Seq. Listing Copy 1 and Seq. Listing Copy 2) and a computer-readable form of the sequence listing, all on CD-ROMs, each containing the file named 38-21(53430)B.ST25.TXT, which is 23.9 MB (measured in MS-DOS) and was created on Aug. 4, 2004, are hereby incorporated by reference.

FIELD OF THE INVENTION

The invention relates to the field of plant molecular biology and plant genetic engineering and more specifically relates to polynucleotide molecules useful for the expression of transgenes in plants. The invention specifically relates to triosephosphate isomerase (TPI) promoter molecules isolated from rice (*Oryza sativa* cv Nipponbare) that are useful for expression of transgenes of agronomic importance in crop plants.

BACKGROUND OF THE INVENTION

One of the goals of plant genetic engineering is to produce plants with agronomically desirable characteristics or traits. Advances in genetic engineering have provided the requisite tools to transform plants to contain and express foreign genes. The technological advances in plant transformation and regeneration have enabled researchers to take an exogenous polynucleotide molecule, such as a gene from a heterologous or native source, and incorporate that polynucleotide molecule into a plant genome. The gene can then be expressed in a plant cell to exhibit the added characteristic or trait. In one approach, expression of a gene in a plant cell or a plant tissue that does not normally express such a gene may confer a desirable phenotypic effect. In another approach, transcription of a gene or part of a gene in an antisense orientation may produce a desirable effect by preventing or inhibiting expression of an endogenous gene.

Promoters are polynucleotide molecules that comprise the 5' regulatory elements, which play an integral part in the overall expression of genes in living cells. Isolated promoters that function in plants are useful for modifying plant phenotypes through the methods of genetic engineering. The first step in the process to produce a transgenic plant includes the assembly of various genetic elements into a polynucleotide construct. The construct includes a transcribable polynucleotide molecule (gene of interest) that confers a desirable phenotype when expressed (transcribed) in the plant cells by a promoter that is operably linked to the gene of interest. A promoter in a construct may be homologous or heterologous to the gene of interest also contained therein. The construct is then introduced into a plant cell by various methods of plant transformation to produce a transformed plant cell and the transformed plant cell is regenerated into a transgenic plant. The promoter controls expression of the gene of interest to which the promoter is operably linked and thus affects the characteristic or trait conferred by the expression of the transgene in plants.

For production of transgenic plants with various desired characteristics, it would be advantageous to have a variety of promoters to provide gene expression such that a gene is transcribed efficiently in the amount necessary to produce the desired effect. The commercial development of genetically improved germplasm has also advanced to the stage of introducing multiple traits into crop plants, often referred to as a gene stacking approach. In this approach, multiple genes conferring different characteristics of interest can be introduced into a plant. It is often desired when introducing multiple genes into a plant that each gene is modulated or controlled for optimal expression, leading to a requirement for diverse regulatory elements. In light of these and other considerations, it is apparent that optimal control of gene expression and regulatory element diversity are important in plant biotechnology.

A variety of different types or classes of promoters can be used for plant genetic engineering. Promoters can be classified on the basis of characteristics such as temporal or developmental range, levels of transgene expression, or tissue specificity. For example, a constitutive promoter continuously expresses a gene with minimal regulation. Therefore, promoters referred to as constitutive promoters are capable of transcribing operably linked genes efficiently and expressing those genes in multiple tissues. Different types of promoters can be obtained by isolating the upstream 5' regulatory regions of genes that are transcribed and expressed in the desired manner, e.g., constitutive, tissue enhanced, or developmentally induced.

Numerous promoters, which are active in plant cells, have been described in the literature. These include the nopaline synthase (nos) promoter and octopine synthase (ocs) promoters carried on tumor-inducing plasmids of *Agrobacterium tumefaciens* and the caulimovirus promoters such as the Cauliflower Mosaic Virus (CaMV) 19S or 35S promoter (U.S. Pat. No. 5,352,605), CaMV 35S promoter with a duplicated enhancer (CaMVE35S, U.S. Pat. Nos. 5,164,316; 5,196,525; 5,322,938; 5,359,142; and 5,424,200), and the Figwort Mosaic Virus (FMV) 35S promoter (U.S. Pat. No. 5,378,619). These promoters and numerous others have been used in the creation of constructs for transgene expression in plants. Other useful promoters are described, for example, in U.S. Pat. Nos. 5,391,725; 5,428,147; 5,447,858; 5,608,144; 5,614,399; 5,633,441; 6,232,526; and 5,633,435, all of which are incorporated herein by reference.

While previous work has provided a number of promoters useful to direct transcription in transgenic plants, there is still a great need for novel promoters with beneficial expression characteristics. In particular, there is a need for promoters that are capable of directing expression of exogenous genes in transgenic crop plants at high levels or in particular tissues, organs, or during specific developmental stages of plant growth. Many previously identified promoters fail to provide the patterns or levels of expression required to fully realize the benefits of expression of selected genes in transgenic plants. There is, therefore, a great need in the art of plant genetic engineering for novel promoters for use in economically important crop plants.

Cytosolic triosephosphate isomerase (TPI) (a plastidic form is encoded by a second nuclear gene in rice) was characterized as a single copy gene with constitutive expression. (Xu, Y. et. al., Plant Physiol. 101:683–687, 1993). TPI's expression by only one cytosolically expressed gene and its importance as an enzyme for multiple pathways (Miernyk, J. A., et. al. 1990. In D. T. Dennis, D. H. Turpin, eds., *Plant Physiology, Biochemistry and Molecular Biology*. Longman Scientific & Technical, Harlow, UK pp 77–100.), suggested that TPI might have a constitutive pattern whose promoter/regulatory elements could direct expression of desired transcribable polynucleotide molecules. For example, a promoter useful in a DNA construct to create a transgenic plant expressing a desirable new phenotype, in particular a DNA construct that includes a glyphosate resistant 5-enolpyruvylshikimate-3-phosphate synthase (EPSPS) gene that results in a glyphosate tolerant transgenic plant.

SUMMARY OF THE INVENTION

In one embodiment the present invention provides a promoter comprising a polynucleotide sequence substantially homologous to a polynucleotide sequence selected from the group consisting of SEQ ID NO: 1, 4 and 11 or any fragments, regions, or cis-elements thereof that are capable of regulating transcription of operably linked polynucleotide molecules, wherein the substantially homologous is at least 85%.

In another embodiment, the invention provides a plant expression construct comprising a promoter comprising a polynucleotide sequence substantially homologous to a polynucleotide sequence selected from the group consisting of SEQ ID NO: 1, 4 and 11 or any fragments, regions, or cis-elements thereof, wherein said promoter is operably linked to a transcribable polynucleotide molecule operably linked to a 3' transcription termination polynucleotide molecule, wherein said transcribable polynucleotide molecule is an agronomic gene of interest.

In yet another embodiment, the invention provides a transgenic plant stably transformed with a DNA construct comprising a promoter comprising a polynucleotide sequence substantially homologous to a polynucleotide sequence selected from the group consisting of SEQ ID NO: 1, 4 and 11 or any fragments, regions, or cis-elements thereof, wherein said promoter is operably linked to a transcribable polynucleotide molecule operably linked to a 3' transcription termination polynucleotide molecule, wherein said transcribable polynucleotide molecule is an agronomic gene of interest.

The foregoing and other aspects of the invention will become more apparent from the following detailed description and accompanying drawings.

BRIEF DESCRIPTION OF THE DRAWINGS

FIG. 1: DNA sequence of the rice TPI gene promoter and 5' transcript end (SEQ ID NO: 1, represents basepairs 2–3939 shown in FIG. 1).

| Base Pair Numbers | Description |
|---|---|
| 2-2710 | Promoter DNA fragment (P-Os.TPI) |
| 2711-2820 | Os.TPI leader 5' of intron |
| 2784 (Underlined Twice) | Mutated G To A |
| 2817 (Underlined Twice) | Mutated A To T |
| 2821-3927 | Intron of P-Os.TPI |
| 3928-3936 | Os.TPI leader from 3' of intron |
| 3937-3939 | Start Codon |

Figure 2:
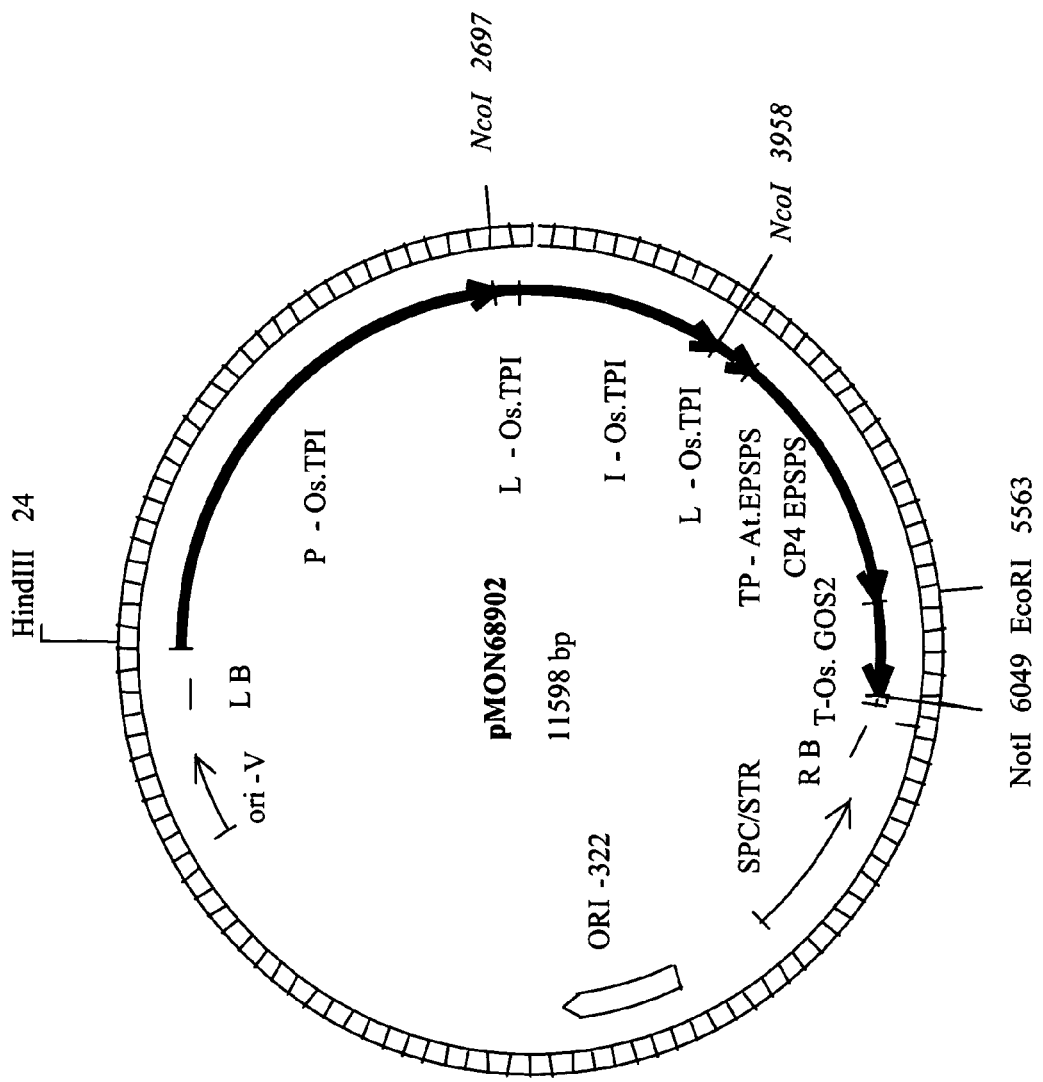

FIG. 2: Illustrates a plasmid map of pMON68902

Figure 3:
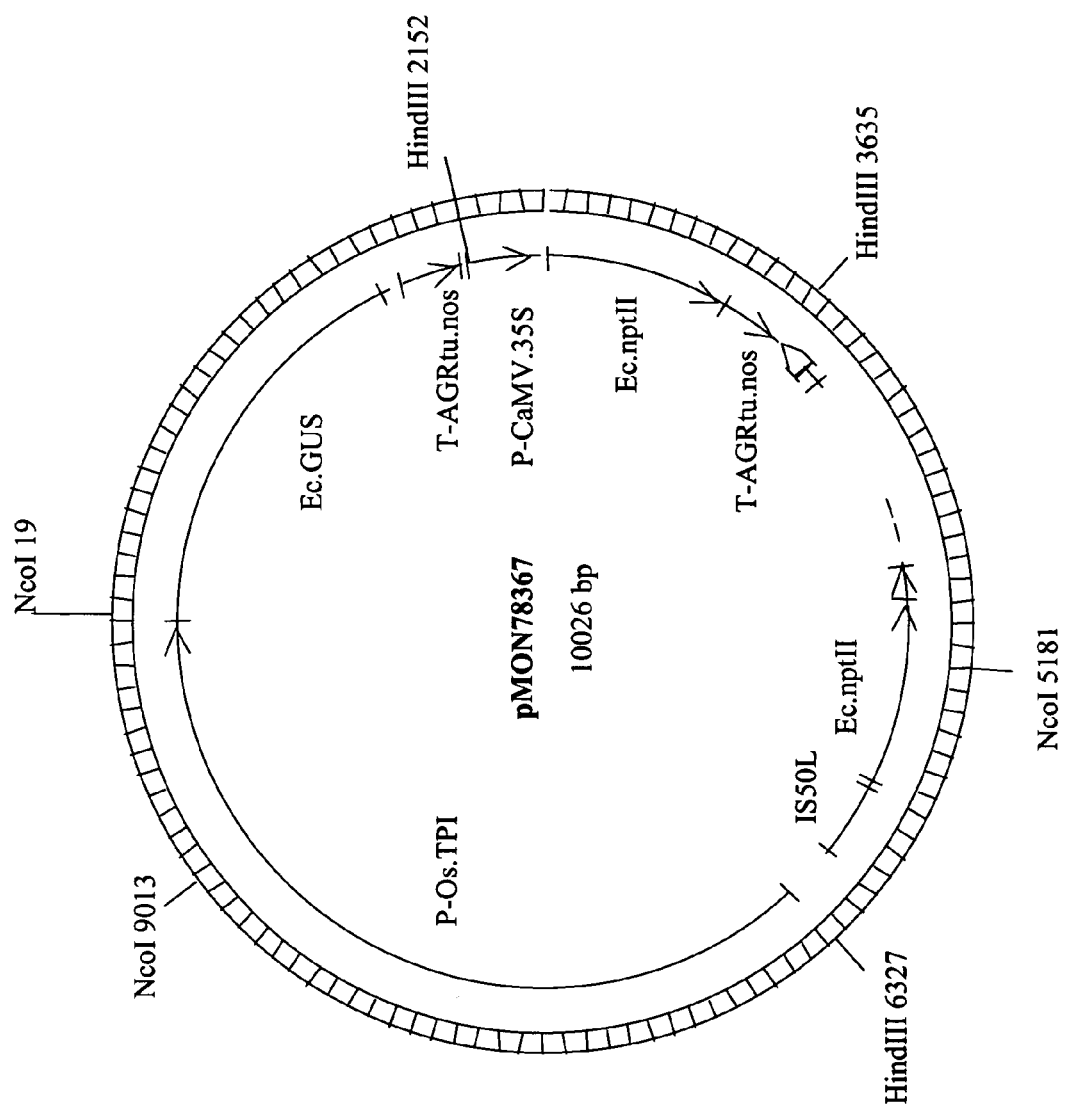

FIG. 3: Illustrates a plasmid map of pMON78367

DETAILED DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the term "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for DNA bases as set forth at 37 CFR § 1.822 is used.

As used herein, the term "promoter" refers to a DNA polynucleotide molecule that in its native state is located upstream or 5' to a translational start codon of an open reading frame (or protein-coding region) and that is involved in recognition and binding of RNA polymerase II and other proteins (trans-acting transcription factors) to initiate transcription. A "plant promoter" is a native or non-native promoter that is functional in plant cells. Constitutive plant promoters are functional in most or all tissues of a plant throughout plant development. Any plant promoter can be used as a 5' regulatory element for modulating expression of a particular gene or genes operably associated thereto. When operably linked to a transcribable polynucleotide molecule, a promoter typically causes the transcribable polynucleotide molecule to be transcribed in a manner that is similar to that of which the promoter is normally associated. In one preferred embodiment, a polynucleotide molecule of the present invention as shown in SEQ ID NO: 1, 4, 11 and 12 and 4 or fragments, variants, or derivatives thereof is incorporated into a construct such that they provide a promoter operably linked to a transcribable polynucleotide molecule that is a gene of interest. This includes a gene that provides a desirable characteristic associated with plant morphology, physiology, growth and development, yield, nutritional enhancement, disease or pest resistance, or environmental or chemical tolerance.

Plant promoters can include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. Thus, the design, construction, and use of chimeric or hybrid promoters comprising at least one cis-element of SEQ ID NO: 1 and 4 for modulating the expression of operably linked polynucleotide sequences is encompassed by the present invention.

As used herein, the term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

In one embodiment, the promoters of the present invention comprise multiple cis-elements each of which confers a different aspect to the overall control of gene expression. In a preferred embodiment, cis-elements from the polynucleotide molecules of SEQ ID NO: 1, 4 and 11 are identified using computer programs designed specifically to identify cis-element, domains, or motifs within sequences. Cis-elements may either positively or negatively regulate gene expression, depending on the conditions. The present invention therefore encompasses cis-elements of the disclosed promoters.

As used herein, the term "substantially homologous" refers to polynucleotide molecules that generally demonstrate a substantial percent sequence identity with the promoters provided herein. Of particular interest are polynucleotide molecules wherein the polynucleotide molecules function in plants to direct transcription and have at least about 85% sequence identity, at least about 90% sequence identity, or even greater sequence identity, such as 98% or 99% sequence identity with the polynucleotide sequences of the promoters described herein. Polynucleotide molecules that are capable of regulating transcription of operably linked transcribable polynucleotide molecules and are substantially homologous to the polynucleotide sequences of the promoters provided herein are encompassed within the scope of this invention.

As used herein, the term "percent sequence identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more polynucleotide sequences may be to a full-length polynucleotide sequence or a portion thereof, or to a longer polynucleotide sequence.

As used herein, the term "homology" refers to the level of similarity or percent identity between polynucleotide sequences in terms of percent nucleotide positional identity, i.e., sequence similarity or identity. As used herein, the term homology also refers to the concept of similar functional properties among different polynucleotide molecules, e.g., promoters that have similar function may have homologous cis-elements. Polynucleotide molecules are homologous when under certain conditions they specifically hybridize to form a duplex molecule. Under these conditions, referred to as stringency conditions, one polynucleotide molecule can be used as a probe or primer to identify other polynucleotide molecules that share homology. The term "stringent conditions" is functionally defined with regard to the hybridization of a nucleic-acid probe to a target nucleic acid (i.e., to a particular nucleic-acid sequence of interest) by the specific hybridization procedure discussed in *Molecular Cloning: A Laboratory Manual,* $3^{rd}$ *edition Volumes* 1, 2, *and* 3. J. F. Sambrook, D. W. Russell, and N. Irwin, Cold Spring Harbor Laboratory Press, 2000 (referred to herein as Sambrook, et al.). Accordingly, the nucleotide sequences of the invention may be used for their ability to selectively form duplex molecules with complementary stretches of polynucleotide molecule fragments. Depending on the application envisioned one would desire to employ varying conditions of hybridization to achieve varying degrees of selectivity of probe towards target sequence. For applications requiring high selectivity, one will typically desire to employ relatively high stringent conditions to form the hybrids, e.g., one will select relatively low salt and/or high temperature conditions, such as provided by about 0.02 M to about 0.15 M NaCl at temperatures of about 50° C. to about 70° C. A high stringent condition, for example, is to wash the hybridization filter at least twice with high-stringency wash buffer (0.2× SSC, 0.1% SDS, 65° C.). Appropriate moderate stringency conditions that promote DNA hybridization, for example, 6.0× sodium chloride/sodium citrate (SSC) at about 45° C., followed by a wash of 2.0×SSC at 50° C., are known to those skilled in the art. Additionally, the salt concentration in the wash step can be selected from a low stringency of about 2.0×SSC at 50° C. to a high stringency of about 0.2×SSC at 50° C. Additionally, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little mismatch between the probe and the template or target strand. Detection of polynucleotide molecules via hybridization is well known to those of skill in the art, and the teachings of U.S. Pat. Nos. 4,965,188 and 5,176,995 are exemplary of the methods of hybridization analyses.

Homology can also be determined by computer programs that align polynucleotide sequences and estimate the ability of polynucleotide molecules to form duplex molecules under certain stringency conditions. Polynucleotide molecules from different sources that share a high degree of homology are referred to as "homologues".

Methods well known to one skilled in the art may be used to identify promoters of interest having activity similar to the promoters described herein. For example, cDNA libraries may be constructed using cells or tissues of interest and screened to identify genes having an expression pattern similar to that of the promoters described herein. The cDNA sequence for the identified gene may then be used to isolate the gene's promoter for further characterization. See for example U.S. Pat. Nos. 6,096,950, 5,589,583 and 5,898,096, incorporated herein by reference. Alternately, transcriptional profiling or electronic northern techniques may be used to identify genes having an expression pattern similar to that of the promoters described herein. Once these genes have been identified, their promoters may be isolated for further characterization. See for example U.S. Pat. Nos. 6,506,565 and 6,448,387, incorporated herein by reference. The electronic northern technique refers to a computer-based sequence analysis which allows sequences from multiple cDNA libraries to be compared electronically based on parameters the researcher identifies including abundance in expressed sequence tag (EST) populations in multiple cDNA libraries, or exclusively to EST sets from one or combinations of libraries. The transcriptional profiling technique is a high-throughput method used for the systematic monitoring of gene expression profiles for thousands of genes. This DNA chip-based technology arrays thousands of cDNA sequences on a support surface. These arrays are simultaneously hybridized to a-multiple of labeled cDNA probes prepared from RNA samples of different cell or tissue types, allowing direct comparative analysis of expression. This approach may be used for the isolation of regulatory sequences such as promoters associated with those genes.

In another embodiment, the promoter disclosed herein can be modified. Those skilled in the art can create promoters that have variations in the polynucleotide sequence. The polynucleotide sequences of the promoters of the present invention as shown in SEQ ID NO: 1 and 4 may be modified or altered to enhance their control characteristics. One preferred method of alteration of a polynucleotide sequence is to use PCR to modify selected nucleotides or regions of sequences. These methods are well known to those of skill in the art. Sequences can be modified, for example by insertion, deletion, or replacement of template sequences in a PCR-based DNA modification approach. A "variant" is a promoter containing changes in which one or more nucleotides of an original promoter is deleted, added, and/or substituted, preferably while substantially maintaining promoter function. For example, one or more base pairs may be deleted from the 5' or 3' end of a promoter to produce a "truncated" promoter. One or more base pairs can also be inserted, deleted, or substituted internally to a promoter. In the case of a promoter fragment, variant promoters can include changes affecting the transcription of a minimal promoter to which it is operably linked. A minimal or basal promoter is a polynucleotide molecule that is capable of recruiting and binding the basal transcription machinery. One example of basal transcription machinery in eukaryotic cells is the RNA polymerase II complex and its accessory proteins. Variant promoters can be produced, for example, by standard DNA mutagenesis techniques or by chemically synthesizing the variant promoter or a portion thereof.

Novel chimeric promoters can be designed or engineered by a number of methods. Many promoters contain cis-elements that activate, enhance or define the strength and/or specificity of the promoter. For example promoters may contain "TATA" boxes defining the site of transcription initiation and other cis-elements located upstream of the transcription initiation site that modulate transcription levels. For example, a chimeric promoter may be produced by fusing a first promoter fragment containing the activator cis-element from one promoter to a second promoter fragment containing the activator cis-element from another promoter; the resultant chimeric promoter may cause an increase in expression of an operably linked transcribable polynucleotide molecule. Promoters can be constructed such that promoter fragments or elements are operably linked, for example, by placing such a fragment upstream of a minimal promoter. The cis-elements and fragments of the present invention can be used for the construction of such chimeric promoters. Methods for construction of chimeric and variant promoters of the present invention include, but are not limited to, combining control elements of different promoters or duplicating portions or regions of a promoter (see for example, U.S. Pat. Nos. 4,990,607; 5,110,732; and 5,097,025, all of which are herein incorporated by reference). Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

In another embodiment, a promoter comprising the polynucleotide sequence shown in SEQ ID NO: 1 and 4 includes any length of said polynucleotide sequence that is capable of regulating an operably linked transcribable polynucleotide molecule. For example, the promoters as disclosed in SEQ ID NO: 1 and 4 may be truncated or portions deleted and still be capable of regulating transcription of an operably linked polynucleotide molecule. In a related embodiment, a cis-element of the disclosed promoters may confer a particular specificity such as conferring enhanced expression of operably linked polynucleotide molecules in certain tissues and therefore is also capable of regulating transcription of operably linked polynucleotide molecules. Consequently, any fragments, portions, or regions of the promoters comprising the polynucleotide sequence shown in SEQ ID NO: 1 and 4 can be used as regulatory polynucleotide molecules, including but not limited to cis-elements or motifs of the disclosed polynucleotide molecules. Substitutions, deletions, insertions or any combination thereof can be combined to produce a final construct.

Polynucleotide Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. Preferably, the two polynucleotide molecules are part of a single contiguous polynucleotide molecule and more preferably are adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, Sambrook, et al.

Constructs of the present invention would typically contain a promoter operably linked to a transcribable polynucleotide molecule operably linked to a 3' transcription termination polynucleotide molecule. Illustrated plasmid maps of the present invention contain various genetic elements that include, but are not limited to: P=promoter; I=Intron; L=5' untranslated region (5' UTR); TP=transit peptide, T=3' untranslated region (3' UTR) plus downstream sequence; SPC/STR=aad, for microbial selection; ori-V and ORI-322 sequences for replication of plasmid in *Agrobacterium tumefaciens* and *Escherichia coli*, respectively; Left T-DNA Border (LB) and Right T-DNA Border (RB) isolated from the Ti plasmid of *Agrobacterium tumefaciens*.

The genetic elements of the DNA construct that enable expression of a new phenotype in transgenic plant cells include the DNA coding sequence of chloroplast transit peptides (CTP). CTP's are engineered to be fused to the coding sequence of the N terminus of a protein. An example would be a prokaryote EPSPS to direct the glyphosate resistant enzymes into the plant chloroplast. In some native plant genes, e.g., EPSPS, chloroplast transit peptide regions are contained in the native coding sequence (e.g., CTP2, Klee et al., Mol. Gen. Genet. 210:47–442, 1987). The native CTP may be substituted with a heterologous CTP during construction of a transgene plant expression cassette. Many chloroplast-localized proteins, including EPSPS, are expressed from nuclear genes as precursors and are targeted to the chloroplast by a chloroplast transit peptide (CTP) that is removed during the import steps. Examples of other such chloroplast proteins include the small subunit (SSU) of Ribulose-1,5,-bisphosphate carboxylase (rubisco), Ferredoxin, Ferredoxin oxidoreductase, the light-harvesting complex protein I and protein II, and Thioredoxin F. It has been demonstrated in vivo and in vitro that non-chloroplast proteins may be targeted to the chloroplast by use of protein fusions with a CTP and that a CTP sequence is sufficient to target a protein to the chloroplast. Incorporation of a suitable chloroplast transit peptide, such as, the *Arabidopsis thaliana* EPSPS CTP (Klee et al., Mol. Gen. Genet. 210:437–442 (1987), and the *Petunia hybrida* EPSPS CTP (della-Cioppa et al., Proc. Natl. Acad. Sci. USA 83:6873–6877 (1986) has been shown to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. Nos. 5,627,061, 5,633,435, 5,312,910, EP 0218571, EP 189707, EP 508909, and EP 924299). Those skilled in the art will recognize that various chimeric constructs can be made that utilize the functionality of a particular CTP to import glyphosate resistant EPSPS enzymes into the plant cell chloroplast.

In addition, constructs may include, but are not limited to additional regulatory polynucleotide molecules from the 3' UTR of plant genes (e.g., a 3' UTR to increase mRNA stability of the mRNA, such as the PI-II termination region of potato or the octopine or nopaline synthase 3' termination regions). Constructs may include but are not limited to the 5' UTR of an mRNA polynucleotide molecule that can play an important role in translation initiation and can also be a genetic component in a plant expression construct. For example, non-translated 5' leader polynucleotide molecules derived from heat shock protein genes have been demonstrated to enhance gene expression in plants (see for example, U.S. Pat. Nos. 5,659,122, 5,362,865, and U.S. Patent Application No. 20020192812). These additional upstream and downstream regulatory polynucleotide molecules may be derived from a source that is native or heterologous with respect to the other elements present on the promoter construct.

Thus, constructs of the present invention comprise promoters such as provided in SEQ ID NO: 1 and 4 or modified as described above, operatively linked to a transcribable polynucleotide molecule so as to direct transcription of said transcribable polynucleotide molecule at a desired level or in a desired tissue or developmental pattern upon introduction of said construct into a plant cell. In some cases, the transcribable polynucleotide molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into constructs of the present invention include, for example, DNA molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or DNA molecule that is introduced into a recipient cell. The type of DNA included in the exogenous DNA can include DNA that is already present in the plant cell, DNA from another plant, DNA from a different organism, or a DNA generated externally, such as a DNA molecule containing an antisense message of a gene, or a DNA molecule encoding an artificial or modified version of a gene.

The promoters of the present invention can be incorporated into a construct using marker genes as described and tested in transient analyses that provide an indication of gene expression in stable plant systems. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable polynucleotide molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Preferred marker genes for transient analyses of the promoters or promoter fragments of the present invention include a GUS gene (U.S. Pat. No. 5,599,670, herein incorporated by reference) or a GFP gene (U.S. Pat. No. 5,491,084, herein incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a polynucleotide molecule of the present invention as shown in SEQ ID NO: 1, 4 and 11 or fragments, variants, or derivatives thereof is incorporated into a construct such that a promoter of the present invention is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding EPSPS described in U.S. Pat. Nos. 5,627,061, 5,633,435, and 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al, (1993) *Plant J.* 4:833–840 and Misawa et al, (1994) *Plant J.* 6:481–489 for norflurazon tolerance; a polynucleotide molecule encoding acetohydroxyacid synthase (AHAS, aka ALS) described in Sathasiivan et al. (1990) *Nucl. Acids Res.* 18:2188–2193 for tolerance to sulfonylurea herbicides; and the bar gene described in DeBlock, et al. (1987) *EMBO J.* 6:2513–2519 for glufosinate and bialaphos tolerance.

The promoter and regulatory elements of the present invention can be linked to other known DNA molecules that encode glyphosate resistant EPSPS enzymes. These other enzymes include, but are not limited to microbial class II EPSP synthases and modified class I EPSP synthases, for example, the modified maize EPSPS gene encoding an EPSPS protein having isoleucine at position 102 and serine at position 106 (U.S. Pat. No. 6,040,497, herein incorporated by reference). The genes that encode enzymes that degrade or inactivate glyphosate are also contemplated to be useful to confer plant tolerance to glyphosate when operably linked to the Asp gene 5' regulatory elements, these include, for example, the glyphosate oxidoreductase and glyphosate-N-acetyl transferase (GOX, U.S. Pat. No. 5,463,175 and GAT, U.S. Patent publication 20030083480, herein incorporated by reference).

In one preferred embodiment, a polynucleotide molecule of the present invention as shown in SEQ ID NO: 1, 4 and 11 or fragments, variants, or derivatives thereof is incorporated into a construct such that a promoter of the present invention is operably linked to a transcribable polynucleotide molecule that is a gene of agronomic interest. As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407, and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Patent Publication No. US20030028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference.

Alternatively, a transcribable polynucleotide molecule can effect the above mentioned phenotypes by encoding a non-translatable RNA molecule that causes the targeted inhibition of expression of an endogenous gene, for example via antisense and inhibitory RNA, or cosuppression-mediated mechanisms. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest is useful for the practice of the present invention.

The constructs of the present invention are generally double Ti plasmid border DNA constructs that have the right border (herein referred to as RB or AGRtu.RB) and left border (herein referred to as LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants And Plant Cells

As used herein, the term "transformed" refers to a cell, tissue, organ, or organism into which has been introduced a foreign polynucleotide molecule, such as a construct. Preferably, the introduced polynucleotide molecule is integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184, all of which are incorporated herein by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), tobacco (*Nicotiana tabacum*), tomato (*Lycopersicon esculentum*), potato (*Solanum tuberosum*), soybean (*Glycine max*), sunflower (*Helianthus* sp), alfalfa (*Medicago sativa*) and members of the genus *Brassica*.

Methods for specifically transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass (*Agrostis*); wheat (*Triticum aestivum*), millet (*Eleusine* sp) and rye (*Secale cereale*)). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Promoter Isolation and DNA Constructs

Cytosolic triosephosphate isomerase (TPI) was characterized as a single copy gene with constitutive expression. The present invention comprises elements of the rice TPI gene including promoter, introns and leaders, for the incorporation into plant expression cassettes. Examination of 3' UTR's from rice EST libraries indicated that most of these libraries contain at least one representative TPI sequence and hence, supported the hypothesis of a broad expression profile (Table 1). Moreover, rice Act1 (U.S. Pat. No. 5,641,876), a known constitutive promoter with a broad expression profile, has a profile where most of the libraries contain at least one representative Act1 sequence. TPI mRNA was then used to BLAST against assembled rice BAC sequences to identify the corresponding genomic sequences. Two BACs, OSM19526 and OSM19525 containing the 5' and 3' portions of the TPI gene, respectively, were found.

TABLE 1

Occurrence of respective 3' UTR's in rice EST libraries

| Library | 5' + 3' reads | Act1 | TPI |
|---|---|---|---|
| panicle, cracking - ¾ open floret | 20,227 | 7 | 5 |
| developing panicle | 7909 | 5 | 4 |
| late anther | 5956 | 14 | 0 |
| developing seed | 7453 | 1 | 2 |
| dry seed | 9362 | 0 | 0 |
| germinating seed | 9743 | 0 | 1 |
| vegetative apex | 7672 | 2 | 0 |
| leaf, 3–5 leaf | 10,040 | 0 | 3 |
| leaf, 3–4 tiller | 9209 | 1 | 4 |
| leaf, elong-boot | 7897 | 1 | 1 |
| root, 3–5 leaf | 10,524 | 2 | 3 |
| root, 3–4 tiller | 10,624 | 1 | 9 |
| root, third tiller - milk | 7481 | 1 | 5 |

The primers OsTPI5-9 (SEQ ID NO: 2) and JY2130 (SEQ ID NO: 3) were used to isolate the 5' region of the TPI gene, including the promoter, the intron and leader segments from genomic DNA (cv Nipponbare) (SEQ ID NO: 1). The amplification process, which was also used to introduce an ectopic translation initiation codon (in the context of an Nco I restriction site, FIG. 1 basepairs 3935–3940), commenced shortly downstream of the first intron and ended approximately 1.5–2 kb immediately upstream of the transcription initiation site (inferred by looking at the longest 5' UTR present in ESTs). This amplification is carried out by using DNA amplification methods for example Polymerase Chain Reaction (PCR) technologies. A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. In PCR, a primer refers to a short oligonucleotide of defined sequence which is annealed to a DNA template to initiate the polymerase chain reaction. The primers and the DNA were incubated in 94° C. 2 minutes, followed by 10 cycles of: 94° C. 15 seconds, 55° C. 30 seconds, 68° C. 4 minutes, followed by 20 cycles of: 94° C. 15 seconds, 55° C. 30 seconds, 68° C. 4 minutes—plus 5 sec per cycle, followed by one cycle of 68° C. 7 min. The Expand Long Template PCR Kit (Roche, Indianapolis, Ind.) was used for the amplification.

The promoter sequence is provided in SEQ ID NO: 4 (FIG. 1 at 2–2710) and a shortened version in SEQ ID NO: 11 (1409–2658 of FIG. 1). The first intron (SEQ ID NO: 5, FIG. 1 at basepair 2821–3927) of the TPI gene, located within the coding sequence near the start of translation, is necessary for high expression levels in monocots when used in the form of a translational fusion with the second exon (Snowden, et al., Plant Mol. Biol. 31:689–692, 1996; Xu, et al., Plant Physiol. 106:459–467, 1994.) The cloned 5' region was mutagenized with oligonucleotides JY2132 (SEQ ID NO: 6) and JY2133 (SEQ ID NO: 7) converting the native translational start codon from ATG to ATA (FIG. 1 at basepair 2784). A second ATG sequence upstream of the first intron was also mutagenized with oligonucleotides JY2135 (SEQ ID NO: 8) and JY2136 (SEQ ID NO: 9), converting it to TTG (FIG. 1 at basepair 2817). As a result, the potential to initiate translation in the short coding region upstream of the first intron was removed, shifting the initiation of translation downstream of the intron to the engineered ATG in the context of an Nco I site (FIG. 1 at basepair 3935–3940). The 5' leader segment is identified in FIG. 1 at basepair 2711–2820. The 3' leader segment is identified in FIG. 1 at basepair 3928–3936.

A DNA construct was then created by digesting the TPI 5' region with Hind III (FIG. 1 at basepair 1-6)/partial Nco I in order to clone it into a Hind III/Nco I cut pMON52244 backbone. A 3' transcriptional termination region from a rice GOS2 gene segment (SEQ ID NO: 10) was added to the DNA construct. The GOS2 3' UTR was ligated (Sambrook et al) onto the 3' end of the desired transgene. For glyphosate tolerance characterization, the plant transformation vector pMON68902, as shown in FIG. 2, contains the CTP2/CP4 EPSPS (U.S. Pat. No. 5,633,435) gene as the transgene of interest.

Example 2

Promoter Characterization in Transient Systems

For GUS activity characterization, the plant transformation vector pMON78367, as shown in FIG. 3, contains the GUS reporter gene (Jefferson et al., Biochem. Soc. Trans. 15: 17–19, 1987) as the transgene of interest.

The plant expression vector pMON78367, using particle bombardment, was used to transform maize callus. The GUS activity was then quantitatively evaluated, through the Mug method for in plant promoter characterization. This method provides a quantitative analysis of the GUS expression in the transgenic plant cells. Total protein is extracted from each sample, measured and concentration adjusted such that each sample contains the same amount of total protein. Total protein is assayed using the BIO-RAD Protein Assay kit. Serial dilutions of BSA protein from 0.05 mg/ml to 0.5 mg/ml are used for the standard curve. The MUG assay uses 500 μl of GUS extraction buffer added to the tissues, and tissues are ground with a TEFLON pestle in 1.5 ml EPPENDORF tubes and centrifuged at 10K RPM for 5 minutes at 4° C. (Beckman GS-15R). Four hundred μl of supernatant is transferred to a fresh 96-deep well plate. The extracts are frozen on dry ice, then stored at −80° C. until use. The MUG assay consisted of generating a standard curve of activity with a serial dilution of 4-methyl umbelliferone (Sigma Chemical Co Cat#M1381, St Louis, Mo.) from 31.2 pmoles to 2000 pmoles. Five μl of each extract is added to a flat bottom 96-well plate (Falcon #3872, BD Biosciences) in duplicate after the plate is read for blanking the background. Two hundred μl of GUS assay solution (0.1M $KPO_4$ pH7.8, 1.0 mM EDTA, 5% glycerol, 10.0 mM DTT, 2 mM 4-methyl umbelliferyl glucuronide, FLUKA #69602) is added to each well and mixed with the samples by pipetting. The Plate is read kinetically on a F-max (Molecular Devices, Sunnyvale Calif.) at 37° C. with the filter pair: excitation-355/emission-460. A typical read consists of 21 readings at 3 minute intervals. GUS activity (pmol/min/mg protein) is calculated based on MUG results and protein results of each sample. 1.5 μl of extracts is added to flat bottom 96-well plate (Falcon) in duplicate. 200 ul of diluted dye reagent is added and mixed with the samples. The absorbance at 595 nm is measured in Spectromax 250 (Molecular Devices, Sunnyvale Calif.) at room temperature after 5 minutes incubation at room temperature.

The results, as displayed in Table 2, show an acceptable level of GUS expression for P-Os.TPI, in this transient system, as compared to the blank vector and another promoter (CaMVE35S).

TABLE 2

| Quantitative Analysis of GUS Activity in Maize Callus | |
| --- | --- |
| Construct | GUS Activity (pmoles/μg protein/hour) |
| Os.TPI pMON 78367 | 19.06 + 4.88 |
| CaMV E35S pMON 77952 | 33.53 + 11.28 |
| Blank Vector pMON 77951 | 1.67 + 0.502 |

Example 3

Promoter Characterization in Transgenic Plants

The construct pMON68902 was used to transform corn, using *Agrobacterium tumefaciens* (U.S. Pat. No. 6,603,061). Approximately, 25 transformed corn plants (event) per construct were generated. The corn events were selected on glyphosate containing medium, transferred to soil and subsequently moved to the greenhouse. The corn events were sprayed with glyphosate (0.84 kg acid equivalents $ha^{-1}$) using the Roundup® Ultra (Monsanto Company, St. Louis, Mo.) formulation at approximately the V4 leaf stage. The corn events that survived without injury (<10% chlorosis and malformation) were kept and transferred to large pots. At approximately the V8 stage, a second similar glyphosate application was performed. This second spray was to evaluate male reproductive tolerance. The corn events from pMON68902 were scored for male fertility upon maturation of the tassels. The Male Fertility Rating (MFR) is scored in a range of 1 to 5, where 1 is used when the tassels lacked developed florets (completely sterile) and 5 is used when there are fully developed anthers with pollen shed (fertile; MFR=4–5 is considered commercially viable). A combination of Taqman® (Applied Biosystems, Foster City, Calif.) and Southern (Sambrook et al.) analysis were used to evaluate the transgene copy number in the events going to the greenhouse. Southern analysis using the new elements also showed that these heterologous sequences do not exhibit cross hybridization to endogenous maize sequences—a significant quality for event characterization. These early evaluations are part of a process to select constructs equivalent to the double expression cassette construct, pMON30167 (U.S. patent application Ser. No. 09/682,597). Important criteria for a successful construct include good transformation efficiency (number of events produced/number of explants inoculated) and the ability to reproducibly provide vegetative and reproductive tolerant transformants carrying a single copy of the transgene. A summary of the current construct status is shown in Table 3. In comparison to P-Os.Act1/P-CaMVE35S (pMON30167) the positive control, P-Os.TPI's results demonstrate a surprising ability to confer glyphosate tolerance, as shown by the strong vegetative and reproductive tolerance. Those single copy events that passed greenhouse evaluations were advanced to field evaluations.

TABLE 3

Transformation and Greenhouse Vegetative and Male Fertility Evaluations

| Construct | Transformation Frequency (%) | # Events | Single Copy (%) | Single Copy Vegetatively Tolerant (%) | Single Copy, Vegetatively Tolerant and MFR = 4–5 (%) |
|---|---|---|---|---|---|
| P-Os.Act1/ P-CaMVE35S pMON30167 | 5.1 | 24 | 33 | 21 | 21 |
| P-Os.TPI pMON68902 | 3.0 | 32 | 53 | 53 | 53 |

The field evaluations were performed with F2 generation corn plants. The plants were treated with two applications, at the V4 and V8 stage, of 3.36 kg glyphosate acid equivalents in Roundup® UltraMax formulation (4× above current field use rate). Ten days after each treatment chlorosis and malformation ratings were taken. The male fertility rating was taken at tassel maturity. Commercial event nk603 (pMON25496 containing P-Os.Act1/CP4 EPSPS:P-CaMVE35S/CP4 EPSPS, U.S. patent application Ser. No. 09/872,051) was used as a control standard to evaluate performance of the expression cassette containing the rice TPI (Os.TPI) promoter. The results are shown in Table 4 and demonstrate that the Os.TPI promoter used in pMON68902 provides events with glyphosate tolerance at least equal to the commercial standard event, nk603. The nk603 event contains two plant expression cassettes, therefore the single P-Os TPI expression cassette provides an unexpected high level of glyphosate tolerance to transgenic corn plants.

TABLE 4

Field Evaluation for Vegetative and Male Fertility

| Construct | # Events | Events that Pass V8 Malformation Rating | Events that pass V8 chlorosis rating | Events that pass vegetative ratings and MFR = 4–5 |
|---|---|---|---|---|
| P-Os.Act1 + CaMVE35S pMON25496 | nk603 | nk603 | nk603 | nk603 |
| P-Os.TPI pMON68902 | 7 | 4 | 4 | 4 |

The rice TPI promoter was additionally shown to direct expression of the CP4 EPSPS coding sequence in tobacco plants and provide tobacco plants that are tolerant to glyphosate. A shortened version of the promoter molecule (SEQ ID NO: 11) (about nucleotide position 1409–2658 of FIG. 1) was operably linked to a dicot intron and to the CP4 EPSPS coding sequence and a 3' termination region. Transformation of this expression cassette into tobacco cells and assay of regenerated plants demonstrated that 100 percent of the transgenic plants containing the rice TPI promoter driving expression of a glyphosate resistant EPSPS were vegetatively tolerant and 57 percent of the plants were reproductively tolerant.

We claim:

1. An isolated promoter comprising SEQ ID NO:1 or consisting of a polynucleotide sequence selected from the group consisting of SEQ ID NO:1, 4, 11, and fragments of SEQ ID NO:1 comprising SEQ ID NO:11, wherein said isolated promoter is capable of regulating transcription of an operably linked transcribable polynucleotide molecule.

2. A DNA construct comprising the promoter according to claim 1, that functions in plant cells, wherein said promoter is operably linked to a transcribable polynucleotide molecule operably linked to a 3' transcription termination polynucleotide molecule, wherein said transcribable polynucleotide molecule is a heterologous nucleic acid of agronomic interest.

3. The DNA construct of claim 2, wherein said transcribable polynucleotide molecule confers disease resistance to a transformed plant comprising said construct.

4. The DNA construct of claim 2, wherein said transcribable polynucleotide molecule confers enhanced root growth to a transformed plant comprising said construct.

5. The DNA construct of claim 2, wherein said transcribable polynucleotide molecule confers insect resistance to a transformed plant comprising said construct.

6. The DNA construct of claim 2, wherein said transcribable polynucleotide molecule confers herbicide tolerance to a transformed plant comprising said construct.

7. The DNA construct of claim 2, wherein said transcribable polynucleotide molecule confers stress tolerance to a transformed plant comprising said construct.

8. The DNA construct of claim 2, wherein said transcribable polynucleotide is a nucleic acid that confers glyphosate tolerance to a transformed plant comprising said construct.

9. The DNA construct of claim 2, wherein said 3' transcription termination polynucleotide molecule is the GOS2 3' UTR consisting of SEQ ID NO: 10.

10. A transgenic plant stably transformed with the construct according to claim 2.

11. The transgenic plant of claim 10, wherein said plant is a monocotyledonous plant selected from the group consisting of wheat, maize, rye, rice, oat, barley, turfgrass, sorghum, millet and sugarcane.

12. The transgenic plant of claim 10, wherein said plant is a dicotyledonous plant selected from the group consisting of tobacco, tomato, potato, soybean, cotton, canola, sunflower and alfalfa.

13. The transgenic plant of claim 10, wherein said transcribable polynucleotide molecule confers disease resistance to said transgenic plant.

14. The transgenic plant of claim 10, wherein said transcribable polynucleotide molecule confers enhanced root growth to said transgenic plant.

15. The transgenic plant of claim 10, wherein said transcribable polynucleotide molecule confers insect resistance to said transgenic plant.

16. The transgenic plant of claim 10, wherein said transcribable polynucleotide molecule confers herbicide tolerance to said transgenic plant.

17. The transgenic plant of claim 10, wherein said transcribable polynucleotide molecule confers stress tolerance to said transgenic plant.

18. A seed of said transgenic plant of claim 10, wherein said seed comprises said construct.

* * * * *

UNITED STATES PATENT AND TRADEMARK OFFICE
CERTIFICATE OF CORRECTION

| | | |
|---|---|---|
| PATENT NO. | : 7,132,528 B2 | Page 1 of 1 |
| APPLICATION NO. | : 10/911373 | |
| DATED | : November 7, 2006 | |
| INVENTOR(S) | : Gregory R. Heck, Jinsong You and Scott R. Baerson | |

It is certified that error appears in the above-identified patent and that said Letters Patent is hereby corrected as shown below:

Claim 8, column 29, line 41, after "polynucleotide" insert --molecule--.

Signed and Sealed this

Ninth Day of January, 2007

JON W. DUDAS
*Director of the United States Patent and Trademark Office*

SEQUENCE LISTING

```
<160> NUMBER OF SEQ ID NOS: 11

<210> SEQ ID NO 1
<211> LENGTH: 3938
<212> TYPE: DNA
<213> ORGANISM: Oryza sativa

<400> SEQUENCE: 1
agctttaata ttacaaattt taaataaata aatttatttc ttattttaaa gtaactttta      60
tattaaattt ttcgtacgga acatacggtt tagtagttta attttttttc cgacgtagaa     120
tctgcatatt cattagaaaa gaacgggcta gttgttgagt ccactataga ctcttaaata     180
ggccatgtta gagaaaaacg atagttctgt aaaggccggc tttctgatcg tctctctact     240
agtaatacgc aataattaaa ttcttgtagc aagtgccatg attttctaca ttttggatct     300
```

-continued

```
aaatacgtga cttttcttgt agatggacta tacaacggcc gttgcttatc tcgtctgctc      360
ttgtttttct cgttgtgagc cggtgtcagg ctgatggcat gcaaaacatc cctgcatgca      420
tcttccttct tggttctttc tcttccacat catcaaattt gtttacataa taataaatag      480
agcgcatctt ccttctttgt ttctttctct tccacatcat caaatttatt tacttaacaa      540
taaatagagc ccattgatta ataccttttgt acatgccctt acgcgggaag gaatcgacga     600
caatggtgcg catggaccaa cgtggctata catcagcgac gacaactcac aaccgcgaag      660
caatgtaaac gcagtagcat ctaaataggt aacgacaaag atgttcacta atctccaatt      720
tgtagtttgt agctagtagc atatcatccc agacgggcat atcgcggtta taaataacca      780
gcgatggtcc aattagtttg tccaattact ttcacgagtt aatcccgatc attccaggat      840
taatatatag caggtgcaca atacacatcg gtctcaaacg gccttccttt tagacaacta      900
attatacaag agatatgtaa ttaattaggt gaacccatcg atcaaaagca tcacgacctt      960
acctatagag ctaaagcctc caatggcgag agagttggtg agtaaagagc agatgacaca    1020
gaacgcatat gtacacatga ttgtttcttc tagacgatgg tctttcctgg cttgaataat    1080
gatgttttat agtagtattc cactaataat taataaatat ccctagttgg tcatcttccc    1140
gacgactaag cggtcaacct aagcactcaa cagctactag tactaatgaa tgtcgatctg    1200
catgtgcttc ctgatgtgac actaatgatt gattaattta agactatatg atgttgaaga    1260
ttgaaccacc caaattctct acccatttat atttattccc taatacaatg aagcatgcat    1320
ttatttctag actagagaca tttaattatt ttgccactct taaatgtggt aagtaaccat    1380
ttaccatgta tacccacatg tcatagacac gtaaggatcc aaatgttaac acataggtgt    1440
cagatagtta aacgtctaac ctaaaagtaa caaatattta aatatccctt atatctatga    1500
ttgaaaggaa aaaagtctaa gtacaattgt cgagatatgg caggtttggt aggtctctaa    1560
cttctcaact taactcaaat aattaagttt agagtggaat tatggagcac cttgaatcca    1620
gattcatctc tctaatttgt tttaatagca ctgctctact cccttttaga tggaattgaa    1680
atcgtttggt tggacttcat ccctaacctc cataagaggt gaaattggag ctagaagtat    1740
gtcaaacatg gccatataat ctaagaacag cttatcgaga tatccaacaa aaaataatcg    1800
ttctcctatt tcagtgagta aaaacctgat ggtccaaacg agttgggctg aaaatgggac    1860
agtgtttcgg tgagacgggc ccagcaagaa cataggcctg gttgggcccc tattcccct     1920 acgttttctc ggcccaccca ccgttgggct cggctcgggc ctaccatcgg cggagagga     1980 ggcccaactc gggaaaaagg agaaacagaa aagaggccga aaaggcgaaa gggatcgatg    2040
aggtggggac caccggacca gcgagagatg cgcatcccga tgcagcacga tgccgcggcg    2100
ccctctgttc cgctccgcgc cgcggccacg aaaaccacga cgccgccggg atcatctgcg    2160
tccgccttac cagtggccgt cgctgctatg gatgacttaa gcagttttt ttatgtgtat     2220 aaataaaaca gggtagttaa cgagtcatac tttggttctg gaagagaata tcttttagg     2280 aaaaaagcaa taggtcatct tactctttgc tacaggtgca ataatttgcc cggacaatag    2340
acctgagtat agtttattta gttctaaaca atgcatcaga atatgaggga aaaagatggc    2400
cttagtatag gatcaattga gatgtacagt taaacaaaaa agtagatatg gatttacaaa    2460
attgatgcgg aatattatat ccatgtagta gctcccatgt actagtttct tttgcttgaa    2520
aaaataaaag aagcagataa tttctagaga agtccagaga ataaaaagat tggtggtggg    2580
agtgggaccc acctgtcatt gtcggaggag cctgcctcgc tcatgtgat cccatcggag     2640 gccacacctc tgctccccct atattatcct gtccatggtg ttttttcttcc tcctccacaa   2700
```

```
aaaccaaaat ccaatctcca gctctcttcc cccccccccc cccccccgcgt ccagttccat    2760 ctaatcagct tctcgtcgag ataggccgca agttcttcgt tggtggcaac tggaattgcg    2820 taatttttt ctcttcctgc ttgaaatctc tagtcgcatg ttcttgtgtc tcggtgactc    2880
aggagaattt ttgatttttt tttctgttct ggaacgcgat ttagggagtg ttcgttaggt    2940
ggagatagga gagattgtct ctcgttttcc gcgcgcacgc ttttcaaact actaaacggt    3000
gcgttttttg caaaaaattt caataggaaa gttgctttaa aaaatcatat taatccattt    3060
ttgaaattta aaatagttaa tactcaatta atcatgagct aatggcttac ctcgttttgc    3120
gtatcttccc aatctcctca atccccttct cttcaaacac tcccttagtg atttaagggt    3180
ggagattgcc atgaagggga tggatctttt ttttttttctt gaaacattag gagagatttt    3240
tccacgctga tccagatcgg tgtagaaacc accctggttg gttgagaaga atggatggat    3300
ggcggggttt ttgagatccg gataatatat ctgaagattt ggtcttcgtt ttcagtccgg    3360
tcctaatcct aggaaccaga tgcgattagc tgctacatat gctactccta cacgattagc    3420 cgcgttttt ggcgtttcaa cgcgagacac tcttagtggg aaatttggag ttcactgatc    3480
ttcaggtgtt ccatcttgcg caaagtgtga tgtcgggtat gtttagctcg gttcagactt    3540
cagagtctga aacttttatg aggtgcatgc gtgtattatc cagtgtctag aatttgtctc    3600
tgacgtgaat tatcaagtgt ctagaattta agtcagatca aggagccaac acccggagat    3660
ttattaatca aatggtgcat attagctttt gtcaatcgtg atttctagct ttgaactgtt    3720
gttaacttac acaagaaacg cgtcatgcac ttggagaacg gtagtggtat tgatgcttct    3780
tgtcgaattt ctcgtatgca tatatgctga gaaatgcgaa agaaaagcac gggtattttg    3840
tgtgatttca atgtcgtagt gtggtctgta tcaatcttca aatatttgct tgctaaagac    3900
tgacatgatt cattttgatg taatagaacg ggaccatg                            3938

<210> SEQ ID NO 2
<211> LENGTH: 28
<212> TYPE: DNA
<213> ORGANISM: Oryza sativa

<400> SEQUENCE: 2
aatgaagatt aagattaagc aagggcac                                        28

<210> SEQ ID NO 3
<211> LENGTH: 33
<212> TYPE: DNA
<213> ORGANISM: Oryza sativa

<400> SEQUENCE: 3
ttttttttcc atggtcccgt tctattacat caa                                  33

<210> SEQ ID NO 4
<211> LENGTH: 2709
<212> TYPE: DNA
<213> ORGANISM: Oryza sativa

<400> SEQUENCE: 4
agctttaata ttcaaatttt taaataaata aatttatttc ttattttaaa gtaactttta    60
tattaaattt ttcgtacgga acatacggtt tagtagttta attttttttc cgacgtagaa    120
tctgcatatt cattagaaaa gaacgggcta gttgttgagt ccactataga ctcttaaata    180
ggccatgtta gagaaaaacg atagttctgt aaaggccggc tttctgatcg tctctctact    240
```

-continued

| | |
|---|---|
| agtaatacgc aataattaaa ttcttgtagc aagtgccatg attttctaca ttttggatct | 300 |
| aaatacgtga cttttcttgt agatggacta tacaacggcc gttgcttatc tcgtctgctc | 360 |
| ttgttttttct cgttgtgagc cggtgtcagg ctgatggcat gcaaaacatc cctgcatgca | 420 |
| tcttccttct tggttctttc tcttccacat catcaaattt gtttacataa taataaatag | 480 |
| agcgcatctt ccttctttgt ttctttctct tccacatcat caaatttatt tacttaacaa | 540 |
| taaatagagc ccattgatta ataccttgt acatgccctt acgcgggaag gaatcgacga | 600 |
| caatggtgcg catggaccaa cgtggctata catcagcgac gacaactcac aaccgcgaag | 660 |
| caatgtaaac gcagtagcat ctaaataggt aacgacaaag atgttcacta atctccaatt | 720 |
| tgtagtttgt agctagtagc atatcatccc agacgggcat atcgcggtta taaataacca | 780 |
| gcgatggtcc aattagtttg tccaattact ttcacgagtt aatcccgatc attccaggat | 840 |
| taatatatag caggtgcaca atacacatcg gtctcaaacg gccttccttt tagacaacta | 900 |
| attatacaag agatatgtaa ttaattaggt gaacccatcg atcaaaagca tcacgacctt | 960 |
| acctatagag ctaaagcctc caatggcgag agagttggtg agtaaagagc agatgacaca | 1020 |
| gaacgcatat gtacacatga ttgtttcttc tagacgatgg tctttcctgg cttgaataat | 1080 |
| gatgttttat agtagtattc cactaataat taataaatat ccctagttgg tcatcttccc | 1140 |
| gacgactaag cggtcaacct aagcactcaa cagctactag tactaatgaa tgtcgatctg | 1200 |
| catgtgcttc ctgatgtgac actaatgatt gattaattta agactatatg atgttgaaga | 1260 |
| ttgaaccacc caaattctct acccatttat atttattccc taatacaatg aagcatgcat | 1320 |
| ttatttctag actagagaca tttaattatt ttgccactct taaatgtggt aagtaaccat | 1380 |
| ttaccatgta tacccacatg tcatagacac gtaaggatcc aaatgttaac acataggtgt | 1440 |
| cagatagtta aacgtctaac ctaaaagtaa caaatattta aatatccctt atatctatga | 1500 |
| ttgaaaggaa aaaagtctaa gtacaattgt cgagatatgg caggtttggt aggtctctaa | 1560 |
| cttctcaact taactcaaat aattaagttt agagtggaat tatggagcac cttgaatcca | 1620 |
| gattcatctc tctaatttgt tttaatagca ctgctctact ccctttaga tggaattgaa | 1680 |
| atcgtttggt tggacttcat ccctaacctc cataagaggt gaaattggag ctagaagtat | 1740 |
| gtcaaacatg gccatataat ctaagaacag cttatcgaga tatccaacaa aaaataatcg | 1800 |
| ttctcctatt tcagtgagta aaaacctgat ggtccaaacg agttgggctg aaaatgggac | 1860 |
| agtgtttcgg tgagacgggc ccagcaagaa cataggcctg gttgggcccc tattccccct | 1920 |
| acgttttctc ggcccacca ccgttgggct cggctcgggc ctaccatcgg gcggagagga | 1980 |
| ggcccaactc gggaaaaagg agaaacagaa aagaggccga aaggcgaaa gggatcgatg | 2040 |
| aggtggggac caccggacca gcgagagatg cgcatcccga tgcagcacga tgccgcggcg | 2100 |
| ccctctgttc cgctccgcgc cgcggccacg aaaaccacga cgccgccggg atcatctgcg | 2160 |
| tccgccttac cagtggccgt cgctgctatg gatgacttaa gcagttttt ttatgtgtat | 2220 |
| aaataaaaca gggtagttaa cgagtcatac tttggttctg aagagaata tcttttagg | 2280 |
| aaaaaagcaa taggtcatct tactctttgc tacaggtgca ataatttgcc cggacaatag | 2340 |
| acctgagtat agtttattta gttctaaaca atgcatcaga atatggagga aaagatggc | 2400 |
| cttagtatag gatcaattga gatgtacagt taaacaaaaa agtagatatg gatttacaaa | 2460 |
| attgatgcgg aatattatat ccatgtagta gctcccatgt actagtttct tttgcttgaa | 2520 |
| aaaataaaag aagcagataa tttctagaga agtccagaga ataaaagat tggtggtggg | 2580 |
| agtgggaccc acctgtcatt gtcggaggag cctgcctcgc ctcatgtgat cccatcggag | 2640 |

| | |
|---|---|
| gccacacctc tgctccccct atattatcct gtccatggtg ttttcttcc tcctccacaa | 2700 |
| aaaccaaaa | 2709 |

<210> SEQ ID NO 5
<211> LENGTH: 1107
<212> TYPE: DNA
<213> ORGANISM: Oryza sativa

<400> SEQUENCE: 5

| | |
|---|---|
| gtaattttt tctcttcctg cttgaaatct ctagtcgcat gttcttgtgt ctcggtgact | 60 |
| caggagaatt tttgatttt ttttctgttc tggaacgcga tttagggagt gttcgttagg | 120 |
| tggagatagg agagattgtc tctcgttttc cgcgcgcacg cttttcaaac tactaaacgg | 180 |
| tgcgttttt gcaaaaaatt tcaataggaa agttgcttta aaaaatcata ttaatccatt | 240 |
| tttgaaattt aaaatagtta atactcaatt aatcatgagc taatggctta cctcgttttg | 300 |
| cgtatcttcc caatctcctc aatccccttc tcttcaaaca ctcccttagt gatttaaggg | 360 |
| tggagattgc catgaagggg atggatcttt tttttttct tgaaacatta ggagagattt | 420 |
| ttccacgctg atccagatcg gtgtagaaac caccctggtt ggttgagaag aatggatgga | 480 |
| tggcggggtt tttgagatcc ggataatata tctgaagatt tggtcttcgt tttcagtccg | 540 |
| gtcctaatcc taggaaccag atgcgattag ctgctacata tgctactcct acacgattag | 600 |
| ccgcgttttt tggcgtttca acgcgagaca ctcttagtgg gaaatttgga gttcactgat | 660 |
| cttcaggtgt tccatcttgc gcaaagtgtg atgtcgggta tgtttagctc ggttcagact | 720 |
| tcagagtctg aaactttttat gaggtgcatg cgtgtattat ccagtgtcta gaatttgtct | 780 |
| ctgacgtgaa ttatcaagtg tctagaattt aagtcagatc aaggagccaa cacccggaga | 840 |
| tttattaatc aaatggtgca tattagcttt tgtcaatcgt gatttctagc tttgaactgt | 900 |
| tgttaactta cacaagaaac gcgtcatgca cttggagaac ggtagtggta ttgatgcttc | 960 |
| ttgtcgaatt tctcgtatgc atatatgctg agaaatgcga agaaaagca cgggtatttt | 1020 |
| gtgtgatttc aatgtcgtag tgtggtctgt atcaatcttc aaatatttgc ttgctaaaga | 1080 |
| ctgacatgat tcattttgat gtaatag | 1107 |

<210> SEQ ID NO 6
<211> LENGTH: 29
<212> TYPE: DNA
<213> ORGANISM: Oryza sativa

<400> SEQUENCE: 6

| | |
|---|---|
| aagaacttgc ggcctatctc gacgagaag | 29 |

<210> SEQ ID NO 7
<211> LENGTH: 29
<212> TYPE: DNA
<213> ORGANISM: Oryza sativa

<400> SEQUENCE: 7

| | |
|---|---|
| cttctcgtcg agataggccg caagttctt | 29 |

<210> SEQ ID NO 8
<211> LENGTH: 32
<212> TYPE: DNA
<213> ORGANISM: Oryza sativa

<400> SEQUENCE: 8

```
ggtggcaact ggaattgcgt aatttttttc tc                                    32
```

<210> SEQ ID NO 9
<211> LENGTH: 32
<212> TYPE: DNA
<213> ORGANISM: Oryza sativa

<400> SEQUENCE: 9

```
gagaaaaaaa ttacgcaatt ccagttgcca cc                                    32
```

<210> SEQ ID NO 10
<211> LENGTH: 468
<212> TYPE: DNA
<213> ORGANISM: Oryza sativa

<400> SEQUENCE: 10

```
gccaaaacca ttgcaaagac tatagtttgg ggtggagtat acttggttgt gtacatgcct      60
gcgtgttcca ttgtacacac aaaacctagc cacctcttga ctcttgagtg tatgcttgtt     120
atccgtgtgt tgaagtttgt aagaggcacc atcactatag atgatggctt gtgtccctct     180
ttcatcaaga ttgaataata tatgctactt tgagagcgct atcctgcttg cctgattgtg     240
ttaatactta catccgtccc acactcccac aatataagga aataaggtat tttggcagtt     300
tagagcaaaa ttcccttata ttttttgggac ggatgtcctc tttttctgcat ttttttatgt   360
tcatatgttc ctgaagagta aggtggatct tgatcaacct gtcggtttat ggtgattgat     420
ttgagtggaa tagaatgggc caacgtccgg catacagtta tgcttcag                  468
```

<210> SEQ ID NO 11
<211> LENGTH: 1250
<212> TYPE: DNA
<213> ORGANISM: Oryza sativa

<400> SEQUENCE: 11

```
cacgtaagga tccaaatgtt aacacatagg tgtcagatag ttaaacgtct aacctaaaag      60
taacaaatat ttaaatatcc cttatatcta tgattgaaag gaaaaaagtc taagtacaat     120
tgtcgagata tggcaggttt ggtaggtctc taacttctca acttaactca ataattaag     180
tttagagtgg aattatggag cacctttgaat ccagattcat ctctctaatt tgttttaata   240
gcactgctct actccctttt agatggaatt gaaatcgttt ggttggactt catccctaac    300
ctccataaga ggtgaaattg gagctagaag tatgtcaaac atggccatat aatctaagaa    360
cagcttatcg agatatccaa caaaaaataa tcgttctcct atttcagtga gtaaaaacct    420
gatggtccaa acgagttggg ctgaaaatgg gacagtgttt cggtgagacg ggcccagcaa    480
gaacataggc ctggttgggc ccctattccc cctacgtttt ctcggcccac ccaccgttgg    540
gctcggctcg ggcctaccat cgggcggaga ggaggcccaa ctcgggaaaa aggagaaaca    600
gaaaagaggc cgaaaaggcg aaagggatcg atgaggtggg gaccaccgga ccagcgagag    660
atgcgcatcc cgatgcagca cgatgccgcg gcgccctctg ttccgctccg cgccgcggcc    720
acgaaaacca cgacgccgcc gggatcatct gcgtccgcct taccagtggc cgtcgctgct    780
atggatgact taagcagttt tttttatgtg tataaataaa acagggtagt taacgagtca    840
tactttggtt ctggaagaga atatcttttt aggaaaaaag caataggtca tcttactctt    900
tgctacaggt gcaataattt gcccggacaa tagacctgag tatagtttat ttagttctaa    960
acaatgcatc agaatatgga ggaaaaagat ggccttagta taggatcaat tgagatgtac   1020
agttaaacaa aaaagtagat atggatttac aaaattgatg cggaatatta tatccatgta   1080
```

```
gtagctccca tgtactagtt tcttttgctt gaaaaaataa aagaagcaga taatttctag    1140
agaagtccag agaataaaaa gattggtggt gggagtggga cccacctgtc attgtcggag    1200
gagcctgcct cgcctcatgt gatcccatcg gaggccacac ctctgctccc               1250
```